United States Patent [19]

Filosa et al.

[11] Patent Number: 4,894,358
[45] Date of Patent: Jan. 16, 1990

[54] THERMAL IMAGING WITH YLIDE DYES

[75] Inventors: Michael P. Filosa, Medfield; Stephen R. Herchen, Duxbury; Cheryl P. Petersen, Acton, all of Mass.

[73] Assignee: Polaroid Corporation, Cambridge, Mass.

[21] Appl. No.: 238,476

[22] Filed: Aug. 31, 1988

[51] Int. Cl.⁴ .............................................. B41M 5/18
[52] U.S. Cl. ..................................... 503/201; 427/150; 427/151; 428/913; 428/914; 503/202; 503/214; 503/218; 503/224
[58] Field of Search ................................ 427/150–152; 428/913, 914; 503/202, 218, 224, 214, 201

[56] References Cited

U.S. PATENT DOCUMENTS

| | | | |
|---|---|---|---|
| 4,369,243 | 1/1983 | Credner et al. | 430/223 |
| 4,405,788 | 9/1983 | Locatell et al. | 546/165 |
| 4,602,263 | 7/1986 | Borror et al. | 503/202 |

*Primary Examiner*—Bruce H. Hess
*Attorney, Agent, or Firm*—Sybil A. Campbell

[57] ABSTRACT

Disclosed is a class of dyes that can be rendered colorless by the application of heat in a silverless imaging system and which have utility in information recording and display, color hard copy and photographic systems. Certain dye ylides, for example, xanthane dye ylides are disclosed which when incorporated in a thin film can be imagewise heated to develop an image by reason of the ylide dye disassociating in the areas where heated and thereby being rendered colorless.

10 Claims, No Drawings

THERMAL IMAGING WITH YLIDE DYES

This invention is concerned with a class of dyes that can be rendered colorless by the application of heat in a silverless imaging system. More particularly, it is directed to certain dye ylides, preferably, xanthene dye ylides which when incorporated in a thin film, can be imagewise heated to develop an image by reason of the ylide dye disassociating in the areas where heated and thereby being rendered colorless. These ylides have utility in information recording and display, color hard copy and photographic systems.

The term "ylide" as here used refers to the —N̄-⑤ + portion of the subject dyes wherein ⑤ + is any suitable moiety that will maintain the desired heat-responsive electronic properties in association with an anion.

BACKGROUND ART

U.S. Pat. No. 4,369,243 Credner e.a., Jan. 18, 1983, shows in a silver halide photographic system the reductive cleavage of a "tailed" sulfilimine dye derivative to release a diffusible dye in the non-exposed areas. However, this patent does not show the particular dye structures here of interest nor that the cleavage of the sulfilimine bond with the proper dye structure can be effected by heat alone with the rendering of the dye irreversibly colorless in the heated areas.

U.S. Pat. No. 4,405,788, Locatell e.a., Sept. 20, 1983, shows related xanthene dye structures in photographic systems but does not show ylides.

THIS INVENTION

In brief compass, this invention comprises a heat responsive recording medium having a recording layer containing a colored dye ylide of the formula

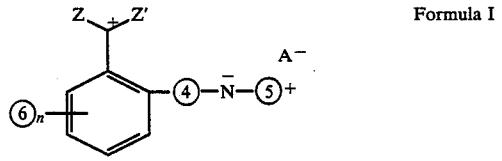

Formula I said dye compound when heated to a temperature above 100° C. cleaves at the —N̄-⑤ + bond with ⑤ departing and with the nitrogen atom bonding to the meso carbon atom to form a 5- or 6-membered ring and rendering the compound colorless, wherein:

Z and Z' taken individually represent the moieties to complete the auxochromophoric system of a triarylmethane dye and Z and Z' when taken together represent the bridged moieties to complete the auxochromophoric system of a bridged triarylmethane dye;

④ is carbonyl, sulfonyl or a methylene or ethylene radical, substituted or unsubstituted;

⑤ + is

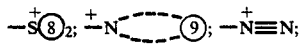

⑥ is hydrogen or a monovalent radical, n being 1, 2, 3, or 4;

⑧ are substituted or unsubstituted aryl groups;

⑨ represents the atoms to complete a heterocyclic ring or ring system, substituted or unsubstituted; and A— is an anion.

Usually, at least one of Z and Z' whether taken individually or together possesses as an auxochromic substituent, a nitrogen, oxygen or sulfur atom or a group of atoms containing nitrogen, oxygen or sulfur.

In the triarylmethane compounds represented in Formula I, the moieties Z and Z', when taken individually, can be the same or different or typically represent heterocyclic groups containing nitrogen, oxygen or sulfur as the heterocyclic atom, particularly N-heterocyclic groups such as julolidin-3-yl, indol-3-yl, pyrr-2-yl, carbazol-3-yl, and indolin-5-yl wherein the N atom of the indolyl, pyrryl, carbazolyl and indolinyl groups may be substituted with hydrogen or alkyl having 1 to 6 carbon atoms, or the moieties Z and Z' typically may be carbocyclic aryl, particularly phenyl or naphthyl groups which include an appropriately positioned auxochromic substituent, i.e., an atom or group that produces an auxochromic effect, which substituent is usually positioned para to the meso carbon atom. Typically, Z and Z' when taken together represent aryl groups bridged by a heteroatom, such as, oxygen, sulfur or nitrogen to form, for example, 4H-chromeno [2,3-C] pyrazole and particularly represent carbocyclic aryl groups, such as, phenyl groups bridged with a heteroatom, preferably oxygen, sulfur or nitrogen and substituted with hydrogen or an alkyl group having 1 to 6 carbon atoms to provide a xanthene, thioxanthene or an acridine dye, respectively, which dyes possess an auxochromic substituent(s) para to the meso carbon atom, i.e., in the 3-position or in the 3,6-positions or meta and para to the meso carbon atom, i.e., in the 3,7-positions.

As is known, the auxochromes are selected to give the dye the desired color and intensity. Examples of useful auxochromic substituents include -OR$_1$ wherein R$_1$ is hydrogen, alkyl usually having 1 to 6 carbon atoms, aralkyl usually having 7 to 15 carbon atoms, alkaryl usually having 7 to 15 carbon atoms or carbocyclic aryl usually having 6 to 12 carbon atoms; —SR$_2$ wherein R$_2$ has the same meaning given for R$_2$; —NR$_3$R$_4$ wherein R$_3$ and R$_4$ each represent hydrogen, alkyl usually having 1 to 6 carbon atoms, β-substituted ethyl, cycloalkyl usually having 5 to 7 carbon atoms, aralkyl usually having 7 to 15 carbon atoms, alkaryl usually having 7 to 15 carbon atoms or

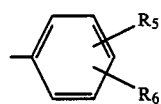

wherein R$_5$ and R$_6$ each are hydrogen, alkyl usually having 1 to 6 carbon atoms, halo such as chloro, bromo, fluoro and iodo, nitro, cyano, alkoxycarbonyl wherein said alkoxy has 1 to 6 carbon atoms, sulfonamido (—NHSO$_2$R$_o$), sulfamoyl (—SO$_2$NHR$_o$), sulfonyl (—SO$_2$R$_o$), acyl (—COR$_o$) or carbamyl (—CONR$_o$) wherein R$_o$ usually is alkyl having 1 to 6 carbon atoms, benzyl or phenyl and R$_3$ and R$_4$ taken together represent the atoms necessary to complete a heterocyclic ring usually piperidino, pyrrolidino, N-methylpiperidino, morpholino or

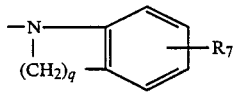

wherein q is an integer 2 to 5 and $R_7$ has the same meaning as $R_5$;

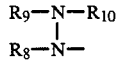

wherein $R_8$ and $R_9$ each are hydrogen, alkyl usually having 1 to 6 carbon atoms or

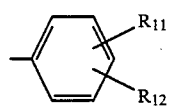

wherein $R_{11}$ and $R_{12}$ have the same meaning as $R_5$ and $R_6$ and $R_{10}$ is $-COR_{13}$, $-CSR_{13}$ or $-SO_2R_{13}$ wherein $R_{13}$ is hydrogen, alkyl usually having 1 to 6 carbon atoms, phenyl, $-NH_2$, $-NHR_{14}$, $-N(R_{14})_2$ or $-OR_{14}$ wherein $R_{14}$ is hydrogen, alkyl usually containing 1 to 6 carbon atoms or phenyl. Representative alkyl groups include methyl, ethyl, propyl, butyl and hexyl. Representative β-substituted ethyl groups include β-methoxymethoxyethyl and β-2'-tetrahydropyranyloxyethyl. Representative aralkyl groups include phenyl and naphthyl-substituted alkyl, such as, benzyl, phenethyl and naphthylmethyl and representative alkaryl groups include alkyl-substituted phenyl and naphthyl, such as o-methylphenyl, o-methylnaphthyl and p-hexylphenyl. Representative carbocyclic aryl groups include phenyl and naphthyl and representative cycloalkyl groups include cyclopentyl, cyclohexyl and cycloheptyl.

Preferred compounds of the present invention are those having the formula

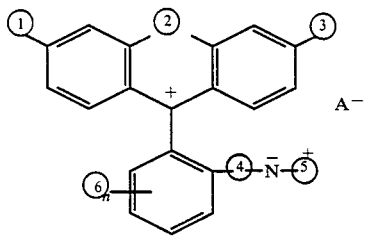

Formula II said dye when heated to a temperature above 100° C. cleaves at the $-\overline{N}$-⑤+ bond with ⑤ departing and with the nitrogen atom bonding to the meso carbon atom to form a 5- or 6-membered ring and rendering the compound colorless, wherein:

① and ③ are auxochromes;
② is a moiety containing a heteroatom;
④ is carbonyl, sulfonyl or a methylene or ethylene radical, substituted or unsubstituted;
⑤+ is

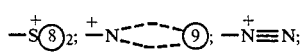

⑥ is hydrogen or a monovalent radical, n being 1, 2, 3 or 4;
⑧ are substituted or unsubstituted aryl groups;
⑨ represents the atoms to complete a heterocyclic ring or ring system, substituted or unsubstituted; and
A— is an anion.

Preferred auxochromes for ① and ③ have the structure:

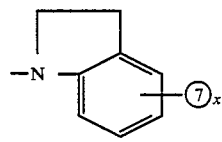

wherein ⑦ is hydrogen or a monovalent radical, x being 1, 2, 3 or 4 and

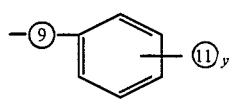

wherein ⑨ is oxygen, sulfur or nitrogen unsubstituted or substituted with, for example, alkyl usually having 1 to 6 carbon atoms, aryl such as phenyl, acyl such as acetyl or

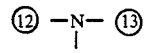

wherein ⑫ is H or alkyl usually having 1 or 6 carbon atoms and ⑬ is acyl such as acetyl and ⑪ is hydrogen or a monovalent radical, y being 1, 2, 3, 4 or 5. Usually the auxochromes ① or ③ are the same.

The monovalent radicals ⑥, ⑦ and ⑪ include radicals such as carboxy; hydroxy; cyano; thiocyano; mercapto; sulfo; nitro; sulfonamido ($-NHSO_2R_o$); sulfamoyl ($-SO_2NHR_o$); sulfonyl ($-SO_2R_o$); acyl ($COR_o$); carbamyl ($-CONR_o$); halomethyl such as trifluoromethyl; alkyl usually having 1 and 20 carbon atoms such as methyl, octyl, hexadecyl; alkoxy usually having 1 to 20 carbon atoms such as methoxy, ethoxy, propoxy and butoxy; alkoxycarbonyl having 1 to 6 carbon atoms such as methoxy- and ethoxycarbonyl; aralkyl usually having 7 to 15 carbon atoms, for example, phenyl or naphthyl-substituted alkyl such as benzyl, phenethyl and naphthylmethyl; alkaryl usually having 7 to 15 carbon atoms, for example, alkyl-substituted phenyl or naphthyl such as o-methylphenyl, o-methylnaphthyl and p-hexylphenyl; aralkyloxy usually having 7 to 15 carbon atoms, for example, phenyl or naphthyl-substituted alkoxy, such as benzyloxy, phenethyloxy and naphthylmethyloxy; aryloxy usually containing 6 to 12 carbon atoms such as phenoxy and naphthoxy; thioalkyl groups usually having 1 to 20 carbon atoms such as methylthio, ethylthio and hexylthio; thioaryl and thioaralkyl groups containing up to 15 carbon atoms such as phenylthio, naphthylthio, benzylthio and phenethylthio; halo such as chloro, bromo, fluoro and iodo; amino including mono- and disubstituted amino such as $-NR'-R''$ wherein R' and R'' each are hydrogen, alkyl usually having 1 to 20 carbon atoms, aralkyl or alkaryl usually having 7 to 15 carbon atoms and carbocyclic aryl usually having 6 to 12 carbon atoms. When n, x and y are greater than 1, the monovalent radicals can be the same or different.

The ②  moiety is preferably oxygen, sulfur or nitrogen, substituted or unsubstituted with an alkyl group usually having 1 to 6 carbon atoms. The ④ moiety is carbonyl, sulfonyl or a methylene or ethylene radical, substituted or unsubstituted.

The aryl groups ⑧ may be substituted or unsubstituted naphthyl or phenyl, the same or different, and usually are phenyl groups, unsubstituted or substituted in the ortho or para positions, or both, with an electron-withdrawing group such as nitro, cyano, methylsulfonyl, phenylsulfonyl, etc.

⑨ represents the atoms to complete a heterocyclic ring or ring system having at least 3 members usually containing 6 to 12 members. Such rings and ring systems include aziridine, pyrazine, piperazine, pyrimidine, quinoline and particularly pyridine and substituted rings and ring systems such as picolines, lutidines, methylethyl pyridines, lepidine, etc.

The anion A— associated with the ylide can be any single atomic ion or ionic group composed of a plurality of atoms having a negative charge, for example, a halide, such as chloride, bromide or iodide, nitrate, tetrafluoroborate, perchlorate, periodate, acetate, oxalate, tosylate, sulfate, methane sulfonate, methane hydrogen disulfonate, m-benzene hydrogen disulfonate, trifluoroacetate, hexafluoroacetate, hexafluorophosphorate, azide or trifluoromethanesulfonate.

The subject compounds may be prepared using conventional techniques by reacting a triarylmethane sulfonyl chloride with the appropriate nucleophile to form the desired ylide. The sulfonyl chloride starting material may be synthesized as described in U.S. Pat. Nos. 4,283,538, 4,290,950 and 4,304,834.

The ylides of this invention usually will be dispersed in a light passing film forming polymer binder, for example, polyvinylpyridine, the film of which may be carried on a suitable support or substrate.

While the ylide compounds of this invention will disassociate with heat alone, the reaction can be enhanced and the activation temperature lowered in many cases by providing a reducing environment, for example, by incorporating certain developers, e.g., phenidone.

Examples

EXAMPLES I–IV:

Four ylides were prepared, Compounds I through IV of the formula wherein the cleavable ⑤+ moiety was varied as indicated in each example.

COMPOUND I

The ⑤+ moiety was

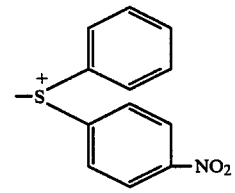

A mixture of benzenethiol 5 g (45.3 mmol), p-fluoronitrobenzene 4.8 ml (45.3 mmol) and potassium carbonate 6.26 g (45.3 mmol) were refluxed in ethanol for 20 hours. The reaction was cooled, concentrated and the solid partitioned between ethyl acetate/water. The organic layer was washed with saturated potassium carbonate and then saturated sodium chloride. It was dried over sodium sulfate and filtered. The solvent was removed under reduced pressure. The residue was recrystallized from hexane and yielded 66%, (6.99 gms) of product, p-nitrophenyl phenyl sulfide.

To a stirred suspension of the p-nitrophenyl phenyl sulfide 3.95 g (1.7 mmol) in methylene chloride at 0° C. was added dropwise a solution of mesithylsulfonyl-o-hydroxylamine 7.36 g (34 mmol) in methylene chloride. The solution was stirred 3 hours at 0° C., refrigerated overnight and then stirred 24 hours at room temperature.

Ethyl ether was added to precipitate the salt, the solvent was decanted and the residue triturated with petroleum ether and refrigerated overnight. Then solid was filtered by suction to give 5.3 g (70%) of the corresponding amino sulfonium salt.

To a suspension of the salt 0.5 g (1.12 mmol) and the xanthene sulfonyl chloride (Compound A) 0.77 g (1.12 mmol), in 10 ml acetone was added potassium carbonate 0.38 g (2.8 mmol) in 1 ml water with stirring at 25° C. After 3 hours the reaction was complete. The solvent was removed under reduced pressure and the residue slurried in water, filtered and washed several times with water and then with aqueous acetone. The solid was dried overnight, then chromatographed on silica gel eluted with 10% methanol/methylene chloride followed by a second silica gel column, eluted with 5% methanol/methylene chloride. The yield was 0.586 gms (64%) of Compound I.

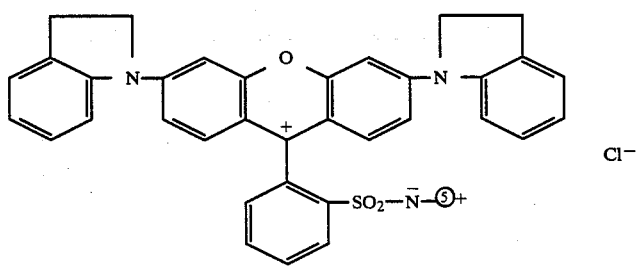

Cl⁻

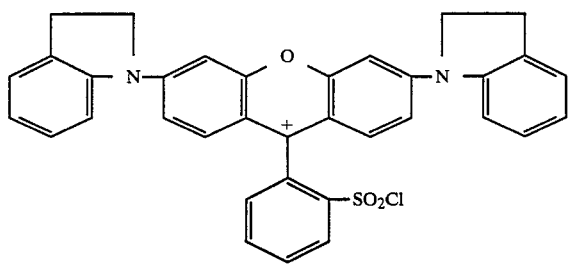

Compound A

COMPOUND II

The ⑤+ moiety was

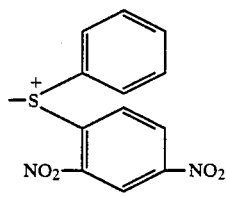

To a stirred mixture of 2,4-dinitrofluorobenzene, 5.69 ml (45 mmol) and potassium carbonate 6.3 g (45 mmol) in acetone was added benzenethiol 4.65 ml (45 mmol). The mixture was heated to reflux for 2 hours, cooled and the solvent removed under reduced pressure. The residue was partitioned between ethyl acetate and water. The organic layer was washed with saturated potassium carbonate, dried over sodium sulfate, filtered and the solvent removed under reduced pressure to give 7.0 g (56%) of 2,4-dinitrophenyl phenyl sulfide.

To a stirred suspension of the 2,4-dinitrophenyl phenyl sulfide, 3.2 g (11.7 mmol) in methylene chloride at 0° C. was added dropwise a solution of mesitylsulfonyl-o-hydroxylamine 5.0 g (23.4 mmol) in methylene chloride. The mixture was allowed to warm to 25° C. and stirred for 12 hours. The solvent was removed under reduced pressure. The resulting precipitate was triturated with ether and the solid filtered and dried to give 1.8 g (31%) of the corresponding amino sulfonium salt.

To a suspension of the amino sulfonium salt 1.0 g (2.03 mmol) and the sulfonyl chloride (Compound A) 1.3 g (2.03 mmol) in 10 ml of acetone was added potassium carbonate 0.7 g (5.07 mmol) in 1 ml of water with stirring at 25° C. After 4.5 hours the acetone was removed under reduced pressure and the residue partitioned between methylene chloride and water. The organic layer was washed with water and saturated sodium chloride and dried over sodium sulfate. It was filtered and the solvent removed under reduced pressure and chromatographed on a silica gel column eluted with 10% methanol/methylene chloride, followed by a second column eluted with 10% methanol/methylene chloride to give 0.31 g (28%) of Compound II.

Mesitylsulfonyl-o-hydroxylamine used in the synthesis of Compounds I and II was prepared in several steps as follows:

To an ice cold solution of acetonitrile, 52 ml (1 mol) distilled from phosphorus pentoxide in ethanol, 71 ml (1.1 mol), was added dry hydrochloric acid until 1.1 moles had been absorbed. The mixture was refrigerated for 72 hours. White crystals deposited on the bottom of the flask. They were filtered, washed with ice cold ether and placed under vacuum to give 40 g (32.3%) of acetimino-ethylester hydrochloride. To a solution of potassium carbonate 89.6 g (0.65 mol) in water cooled to 5° C. in an ice bath was added the iminoester hydrochloride 40 g (0.324 mol) as a solid in several portions over a 5 minute period. The solution was warmed to 25° C. for 10 minutes then extracted with ether 2 times. The combined ether layers were cooled to 5° C. and a solution of hydroxylamine hydrochloride, 28.1 g (0.4 mol), in water was added with stirring over a 10 minute period. The solution was warmed to 25° C. while vigorously stirring for 25 min. The ether layer was separated and dried over sodium sulfate. It was filtered and concentrated under reduced pressure and the residual oil refrigerated giving 19.3 gm (58%) of ethyl acetohydroxamate.

To a solution of the ethyl acetohydroxamate, 15.3 g (0.149 mol) and triethylamine, 20.7 ml (0.149 mol), in dimethylformamide was added powdered 2-mesitylenesulfonyl chloride, 32.58 g (0.148 mol) in small portions over a 20 minute period with stirring at 5° C. The mixture was stirred an additional 20 minutes then poured into ice water. The resulting precipitate was collected and washed with water. The precipitate was dissolved in ether, dried over sodium sulfate, filtered and the solvent removed under reduced pressure. The residue was dissolved in petroleum ether and cooled. The resulting precipitate was filtered and dried over suction and gave 24.65 g (58%) of ethyl-o-(mesitylenesulfonyl)-acetohydroxamate as a powdery white solid melting range 54°–56° C.

To a solution of this oxime 10 g (0.035 mol) in 20 ml dioxane was added 70% perchloric acid, 3.2 ml (0.038 mol), with stirring over a 10 minute period at 0° C. When ⅔ of the acid was added, the mixture became pasty. It was stirred 10 minutes after the addition and slowly poured into ice water. It solidified after 1 hour and was filtered by suction, washed with water and then petroleum ether. The solid was kept under suction for an additional hour and gave 7.36 g (98%) mesitysulfonyl-o-hydroxylamine product.

COMPOUND III

The ⑤+ moiety was

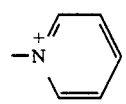

To a stirred solution of 1-aminopyridinium iodide 0.347 g (1.56 mmol) and the sulfonyl chloride (Compound A), 1.0 g (1.56 mmol), in acetone was added potassium carbonate, 0.54 g (3.9 mmol) in 1 ml of water. The mixture was stirred 2 hours at 25° C. The acetone was removed under reduced pressure and the residue dissolved in methylene chloride and washed with water and saturated sodium chloride. It was dried over sodium sulfate, filtered and concentrated under reduced pressure. The product was purified by column chromatography, silica gel eluted with 5% methanol/methylene chloride and rechromatographed on a silica gel plate eluted with 7% methanol/methylene chloride and gave 0.44 g (51%) of pure Compound III.

COMPOUND IV

The  moiety was $$-\overset{+}{N}\equiv N$$

Sodium azide, 20.0 g (0.308 mol), was dissolved in water (200 ml) and added dropwise over 0.5 hours to a solution of the sulfonyl chloride (Compound A) (35 g) dissolved in dry acetonitrile (300 ml) at ambient temperature. The reaction was stirred vigorously for 0.5 hours and the acetonitrile was then removed by rotary evaporation and replaced with methylene chloride (500 ml). A blue solid was filtered from this mixture. This solid was slurried in methylene chloride (500 ml) and hydrogen chloride gas was bubbled through until the solid dissolved. Washing with 100 ml of water 2 times, drying over magnesium sulfate and concentration afforded a very pure sample of the desired sulfonylazide (14.0 g, 0.22 mole, 42% yield) as a blue solid. The original methylene chloride layer was treated similarly with hydrogen chloride gas, washed with water 2 times (100 ml), dried over magnesium sulfate and concentrated to yield a second less pure sample of the sulfonylazide (13.0 g, 0.021 moles, 40% yield) mainly contaminated with minor amounts of the sulfonic acid derived from Compound A. Total yield of Compound IV was 27.0 g (0.043 mole). An analytically pure sample of Compound IV was obtained by flash chromatography on silica gel using a gradient of 0 to 7.5% methanol in methylene chloride.

EXAMPLE V—COMPOUND V

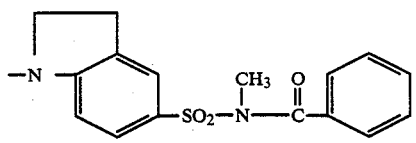

The xanthene sulfonyl chloride starting material (1.02 g, 1.0 mmoles) was added in a single portion to a solution of sodium azide (1.00 g, 15.4 mmoles) in water (10 ml), diluted with acetonitrile (50 ml). After one hour the reaction was quenched with 1N HCl (50 ml) and extracted with methylene chloride (2 times with 100 ml). Drying over magnesium sulfate and concentration afforded a mixture of the sulfonyl azide, Compound V, and the corresponding sulfonic acid. Two flash chromatographies on silica gel using a gradient of 2 to 5% methanol in methylene chloride afforded the desired sulfonylazide dye. Compound V, as a dark blue solid (260 mg, 0.25 mmoles, 25%).

THERMAL BLEACHING

Approximately 5 mgs of the indicated compound was mixed with approximately 5 mgs of poly(4-vinylpyridine) and methanol was added to give a coatable solution. The solution was coated on a rectangular glass plate and the coating dried at room temperature under a stream of nitrogen. Then one-half of the glass plate was placed on a hot plate preheated to a predetermined temperature and color bleaching observed over time.
COMPOUND I—Cyan-colored coating
 (a) 150° C. for 90 seconds—no bleaching of heated area
 (b) 200° C. for 60 seconds—heated area turned colorless
 (c) When phenidone in slight excess over one equivalent was mixed with the dye in the coating, the heated area turned colorless after 90 seconds at 150° C.
COMPOUND III—Cyan-colored coating
 (a) 200° C. for 3 minutes—heated area turned colorless
 (b) When phenidone in slight excess over one equivalent was mixed with the dye in the coating, the heated area turned colorless after 1.5 minutes at 150° C.
COMPOUND V—Cyan-colored coating
 200° C. for 2 minutes—heated area turned colorless.
One advantage of this invention is that the bleaching

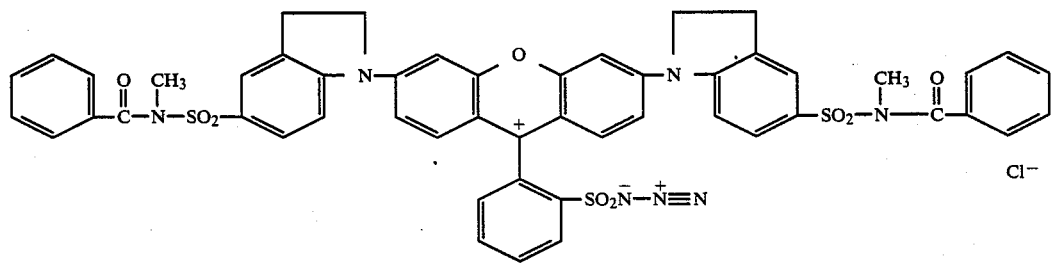

This azide was prepared similarly to Compound IV from the corresponding xanthene sulfonyl chloride except that the auxochrome moieties 1 and 3 were:

is irreversible so that the bleached areas are not prone to colorize in time.

It will be appreciated that the dye precursor compounds used in the present invention can be monomeric or polymeric compounds. Suitable polymeric compounds are those which, for example, comprise a polymeric backbone chain having dye precursor moieties attached directly thereto or through pendant linking groups. Polymeric compounds of the invention can be provided by attachment of the dye precursor moiety to the polymeric chain via the Z and/or Z' moieties or the phenyl ring. For example, a monomeric dye precursor compound having a reactable substituent group, such as an hydroxyl or amino group, can be conveniently reacted with a monoethylenically unsaturated and polymerizable compound having a functional and dervitizable moiety, to provide a polymerizable monomer having a pendant dye precursor moiety.

In producing images according to the present invention, the way in which the heat is applied or induced imagewise may be realized in a variety of ways, for example, by direct application of heat using a thermal printing head or thermal recording pen or by conduction from heated image-markings of an original using conventional thermographic copying techniques. Preferably, selective heating is produced in the image-forming layers by the conversion of electromagnetic radiation into heat and, preferably, the light source is a laser beam emitting source such as a gas laser or semiconductor laser diode. The use of a laser beam is not only well suited for recording in a scanning mode but by utilizing a highly concentrated beam, photoenergy can be concentrated in a small area so that it is possible to record at high speed and high density. Also, it is a convenient way to record data as a heat pattern in a response to transmitted signals such as digitized information and a convenient way of preparing multicolor images by employing a plurality of laser beam sources that emit laser beams of different wavelengths.

In the latter embodiment an infra-red absorbing substance is employed for converting infra-red radiation into heat which is transferred to the subject compound to initiate the bleaching. Obviously, the infra-red absorber should be in heat-conductive relationship with the heat-sensitive compound, for example, in the same layer as the heat-sensitive compound or in an adjacent layer. Preferably, the infra-red absorber is an organic compound, such as a cyanine, merocyanine or thiopyrylium dye and preferably, is substantially non-absorbing in the visible region of the electromagnetic spectrum so that it will not add any substantial amount of color.

In the production of multicolor images, infra-red absorbers may be selected that absorb radiation at different wavelengths above 700 nm, which wavelengths are usually about 40 nm apart. Thus each imaging layer may be exposed independently of the others by using an appropriate infra-red absorber. As an illustration, the yellow, magenta and cyan layers of heat-sensitive ylides may have infra-red absorbers associated therewith that absorb radiation at 760 nm, 820 nm and 1100 nm, respectively, and may be addressed by laser beam sources, for example, infra-red laser diodes emitting laser beams at these respective wavelengths so that the yellow imaging layer can be exposed independently of the magenta and cyan imaging layers, the magenta imaging layer can be exposed independently of the yellow and cyan imaging layers, and the cyan imaging layer can be exposed independently of the yellow and magenta imaging layers. While each layer may be exposed in a separate scan, it is usually preferred to expose all of the imaging layers simultaneously in a single scan using multiple laser beam sources of the appropriate wavelengths. Rather than using superposed imaging layers, the heat-sensitive compounds and associated infra-red absorbers may be arranged in an array of side-by-side dots or stripes in a single recording layer.

In a further embodiment, multicolor images may be produced using the same infra-red absorbing compound in association with each two or more superposed imaging layers and exposing each imaging layer by controlling the depth of focusing of the laser beam. In this embodiment, the concentration of infra-red absorber is adjusted so that each of the infra-red absorbing layers absorb approximately the same amount of laser beam energy. For example, where there are three infra-red absorbing layers, each layer would absorb about one-third of the laser beam energy. It will be appreciated that controlling the focusing depth to address each layer separately may be carried out in combination with the previous embodiment of using infra-red absorbers that selectively absorb at different wavelengths in which instance the concentration of infra-red absorber would not have to be adjusted for the laser beam energy since the first infra-red dye would not absorb any substantial amount of radiation at the absorption peaks of the second and third dyes and so forth.

Where imagewise heating is induced by converting light to heat as in the embodiments described above, the heat-sensitive element may be heated prior to or during imagewise heating. This may be achieved using a heating platen or heated drum or by employing an additional laser beam source for heating the element while it is being exposed imagewise.

The heat-sensitive elements of the present invention comprise a support carrying at least one imaging layer of the above-denoted heat-sensitive compounds and may contain additional layers, for example, a subbing layer to improve adhesion to the support, interlayers for thermally isolating the imaging layers from each other, infra-red absorbing layers as discussed above, anti-static layers, an anti-abrasive topcoat layer which also may function as a UV protecting layer by including an ultraviolet absorber therein or other auxiliary layers. For example, an electroconductive layer may be included and imagewise bleaching effected by heat energy generated in response to an electrical signal.

The heat-sensitive compounds are selected to give the desired color or combination of colors, and for multicolor images, the compounds selected may comprise the additive primary colors red, green and blue, the subtractive primaries yellow, magenta and cyan or other combinations of colors, which combinations may additionally include black. As noted previously, the compounds generally are selected to give the subtractive colors cyan, magenta and yellow commonly employed in photographic processes to provide full natural color.

The support employed may be transparent or opaque and may be any material that retains its dimensional stability at the temperature used for image formation. Suitable supports include paper, paper coated with a resin or pigment, such as, calcium carbonate or calcined clay, synthetic papers or plastic films, such as polyethylene, polypropylene, polycarbonate, cellulose acetate, polyethylene terephthalate and polystyrene.

Usually the layer of heat-sensitive compound contains a binder and is formed by combining the heat-sensitive compound and a binder in a common solvent, applying a layer of the coating composition to the support and then drying. Rather than a solution coating, the layer may be applied as a dispersion or an emulsion. The coating composition also may contain dispersing agents, plasticizers, defoaming agents, coating aids and materials such as waxes to prevent sticking where thermal recording heads or thermal pens are used to apply the imagewise pattern of heat. In forming the layer(s) containing the heat-sensitive compounds and the interlayers or other layers, temperatures should be maintained below levels that will initiate the bleaching reaction so that the heat-sensitive ylides will not be prematurely caused to react.

Any of the binders commonly employed in heat-sensitive recording elements may be employed provided that the binder selected does not have any adverse effect on the heat-sensitive compounds incorporated therein. Also, the binder should be heat-stable at the temperatures encountered during image formation and it should be transparent so that it does not interfere with the viewing of the color image. Where electromagnetic radiation is employed to induce imagewise heating, the binder also should transmit the light intended to initiate image formation. Examples of binders that may be used include polyvinyl alcohol, polyvinyl pyrrolidone, methyl cellulose, cellulose acetate butyrate, copolymers of styrene and butadiene, polymethyl methacrylate, copolymers of methyl and ethyl acrylate, polyvinyl acetate, polyvinyl chloride, polyvinyl butyral and polycarbonate.

Since certain changes may be made in the herein described subject matter without departing from the scope of the invention herein involved, it is intended that all matter contained in the above description and examples be interpreted as illustrative and not in a limiting sense.

What is claimed is:

1. A heat responsive recording medium comprising a support carrying a recording layer comprising a film-forming binder and a colored dye ylide of the formula

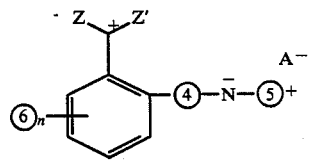

said dye compound when heated to a temperature above 100° C. cleaves at the —N̄-⑤+ bond with ⑤ departing and with the nitrogen atom bonding to the meso carbon atom to form a 5- or 6-membered ring and rendering the compound colorless, wherein:

Z and Z' taken individually represent the moieties to complete the auxochromophoric system of a triarylmethane dye and Z and Z' when taken together represent the bridged moieties to complete the auxochromophoric system of a bridged triarylmethane dye;

④ is carbonyl, sulfonyl or a methylene or ethylene radical, substituted or unsubstituted;

⑤ ± is

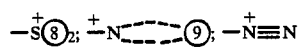

⑥ is hydrogen or a monovalent radical, n being 1, 2, 3, or 4;

⑧ are substituted or unsubstituted aryl groups;

⑨ represents the atoms to complete a heterocyclic ring or ring system, substituted or unsubstituted; and A— is an anion.

2. A thermal imaging method which comprises heating imagewise to a temperature above at least 100° C. the heat responsive recording medium of claim 1 whereby said dye compound is rendered colorless in an imagewise pattern corresponding to said imagewise heating.

3. A heat responsive recording medium comprising a support carrying a recording layer comprising a film-forming binder and a colored xanthene dye ylide of the formula

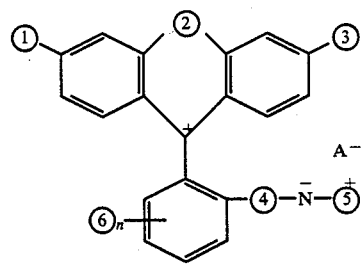

said dye compound when heated to a temperature above 100° C. cleaves at the —N̄-⑤+ bond with ⑤ departing and with the nitrogen atom bonding to the meso carbon atom to form a 5- or 6-membered ring and rendering the compound colorless, wherein:

① and ③ are auxochromes;

② is a moiety containing a heteroatom;

④ is carbonyl, sulfonyl or a methylene or ethylene radical, substituted or unsubstituted;

⑤ + is

⑥ is hydrogen or a monovalent radical, n being 1, 2, 3 or 4;

⑧ are substituted or unsubstituted aryl groups;

⑨ represents the atoms to complete a heterocyclic ring or ring system, substituted or unsubstituted; and A— is an anion.

4. The recording medium of claim 3 wherein ② is oxygen, sulfur or nitrogen, unsubstituted or substituted with alkyl.

5. The recording medium of claim 3 wherein ① and ③ are:

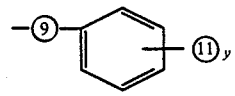

wherein ⑨ is oxygen, sulfur or nitrogen, unsubstituted or substituted; ⑪ is hydrogen or a monovalent radical and y is 1, 2, 3, 4 or 5.

6. The recording medium of claim 3 wherein ① and ③ are:

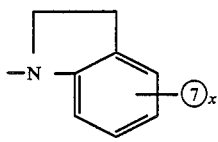
wherein ⑦ is hydrogen or a monovalent radical and x is 1, 2, 3 or 4.
7. The recording medium of claim 3 wherein A⁻ is a halide.
8. The recording medium of claim 3 which additionally includes a reducing agent.
9. The recording medium of claim 8 wherein said reducing agent is phenidone.
10. The recording medium of claim 3 wherein said film-forming polymer binder is a polyvinyl pyridine.